(12) United States Patent
Ellingson et al.

(10) Patent No.: US 10,982,362 B2
(45) Date of Patent: Apr. 20, 2021

(54) NONWOVEN FABRIC SHEET AND METHOD FOR MAKING THE SAME

(71) Applicant: Fibertex Personal Care A/S, Aalborg (DK)

(72) Inventors: Daniel Lee Ellingson, Woodbury, MN (US); Morten Rise Hansen, Aalborg (DK)

(73) Assignee: FIBERTEX PERSONAL CARE A/S, Aalborg (DK)

( * ) Notice: Subject to any disclaimer, the term of this patent is extended or adjusted under 35 U.S.C. 154(b) by 25 days.

(21) Appl. No.: 16/309,118

(22) PCT Filed: Aug. 29, 2017

(86) PCT No.: PCT/EP2017/001027
§ 371 (c)(1),
(2) Date: Dec. 12, 2018

(87) PCT Pub. No.: WO2018/046119
PCT Pub. Date: Mar. 15, 2018

(65) Prior Publication Data
US 2019/0309458 A1    Oct. 10, 2019

(30) Foreign Application Priority Data
Aug. 31, 2016   (EP) .................................... 16186645

(51) Int. Cl.
*D04H 3/018*   (2012.01)
*D01F 8/06*    (2006.01)
(Continued)

(52) U.S. Cl.
CPC ....... *D04H 3/018* (2013.01); *A61F 13/51108* (2013.01); *D01F 8/06* (2013.01);
(Continued)

(58) Field of Classification Search
CPC ...................................................... D04H 3/018
See application file for complete search history.

(56) References Cited

U.S. PATENT DOCUMENTS

| | | | |
|---|---|---|---|
| 4,035,219 A | 7/1977 | Cumbers | |
| 5,296,289 A * | 3/1994 | Collins | .................... D04H 3/14 26/51 |

(Continued)

FOREIGN PATENT DOCUMENTS

| | | |
|---|---|---|
| CN | 101166859 A | 4/2008 |
| EP | 1876275 A1 | 1/2008 |

(Continued)

OTHER PUBLICATIONS

International Search Report and Written Opinion issued in corresponding International Patent Application No. PCT/EP2017/001027 dated Jan. 26, 2018 (12 pages).

(Continued)

*Primary Examiner* — Andrew T Piziali
(74) *Attorney, Agent, or Firm* — Kilyk & Bowersox, P.L.L.C.

(57) ABSTRACT

The invention relates to a patterned spunbonded nonwoven fabric sheet comprising a plurality of spunbonded crimped fibers bonded together at a plurality of bonding points, wherein all fibers of the patterned spunbonded nonwoven fabric sheet are spunbonded crimped fibers and wherein the configuration of the fibers within the sheet is inhomogeneous and varies according to a preferably regular pattern. The invention further relates to a method for forming such patterned spunbonded nonwoven fabric sheet from a flat spunbonded nonwoven fabric sheet starting material. Still further, the invention relates to such flat spunbonded nonwoven fabric sheet starting material.

8 Claims, 5 Drawing Sheets

Figure 1:
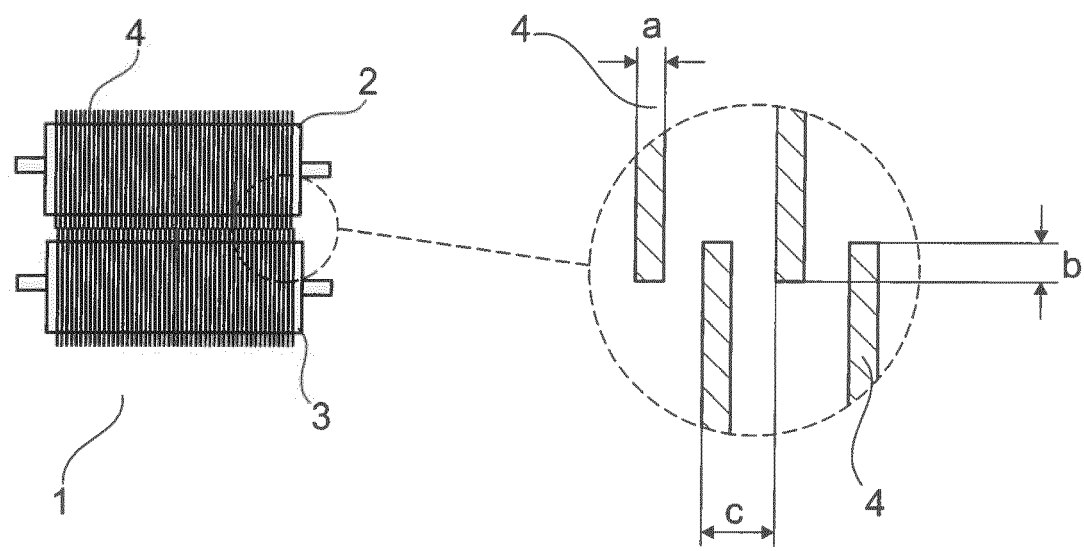

(51) Int. Cl.
  *D04H 3/02* (2006.01)
  *D04H 3/07* (2012.01)
  *A61F 13/511* (2006.01)
  *D06C 3/06* (2006.01)
  *D04H 3/14* (2012.01)
  *B32B 5/02* (2006.01)
  *B44B 5/02* (2006.01)
  *D04H 3/05* (2006.01)
  *D04H 3/16* (2006.01)

(52) U.S. Cl.
  CPC ............... *D04H 3/02* (2013.01); *D04H 3/07* (2013.01); *D04H 3/14* (2013.01); *D06C 3/06* (2013.01); *B32B 5/022* (2013.01); *B44B 5/028* (2013.01); *D04H 3/05* (2013.01); *D04H 3/166* (2013.01)

(56) References Cited

U.S. PATENT DOCUMENTS

| | | | | |
|---|---|---|---|---|
| 6,368,444 | B1* | 4/2002 | Jameson | D04H 13/00 156/229 |
| 2006/0082012 | A1 | 4/2006 | Webb et al. | |
| 2008/0044628 | A1* | 2/2008 | Noda | D04H 1/54 428/163 |
| 2009/0142595 | A1 | 6/2009 | Matsui et al. | |
| 2010/0255255 | A1 | 10/2010 | Kawakami et al. | |
| 2012/0205061 | A1 | 8/2012 | Ducker et al. | |
| 2014/0072767 | A1 | 3/2014 | Klaska et al. | |

FOREIGN PATENT DOCUMENTS

| | | |
|---|---|---|
| EP | 2463428 A1 | 6/2012 |
| JP | 2005120542 A | 5/2005 |
| JP | 2013122104 A | 6/2013 |
| JP | 2014109085 A | 6/2014 |
| WO | 2004038085 A2 | 5/2004 |
| WO | 2004085730 A1 | 10/2004 |
| WO | 2016060238 A1 | 4/2016 |

OTHER PUBLICATIONS

International Preliminary Report on Patentability issued in corresponding International Patent Application No. PCT/EP2017/001027 dated Oct. 2, 2018 (13 pages).

* cited by examiner

NONWOVEN FABRIC SHEET AND METHOD FOR MAKING THE SAME

This application is a National Stage Application of PCT/EP2017/001027, filed Aug. 29, 2017, which claims priority to European Patent Application No. 16186645, filed Aug. 31, 2016.

The invention relates to a patterned spunbonded nonwoven fabric sheet obtained from mechanically activating a flat spunbonded nonwoven fabric sheet comprising a plurality of spunbonded crimped fibers.

Nonwoven fabric materials are known in the art. They made from a plurality of polymer fibers randomly laid onto a surface to form a flat layer and bonded together at a plurality of bonding points to form a flat fabric sheet. Typical processes to obtain such materials comprise spunbonding, a continuous process where thin polymer fibers are spun, drawn and quenched by air streams, randomly dispersed onto a moving belt and bonded by, e.g., calender or hot air through bonding. Spunbonded nonwovens are frequently used in hygiene applications, e.g., as backsheets or leg cuffs for diapers.

Typical nonwoven fabric materials are made from linear fibers, are flat and compact and have a comparatively high density (expressed in g/cm$^3$ of the nonwoven).

There are also technologies available in the prior art to obtain a softer nonwoven fabric materials having much lower densities, so-called high loft nonwoven materials. These technologies use crimped fibers instead of straight fibers to induce loft. Crimped fibers can, for example, be obtained by drawing bicomponent fibers comprising two zones asymmetrically distributed along their cross-section. The zones are constituted by different polymer materials, which are disparate in at least one physical property like melt elasticity, melt flow rate or the like. Such fibers exhibit asymmetric behavior during drawing and quenching, which induces crimp. An exemplary technology is disclosed in U.S. Pat. No. 6,454,989 B1.

The bonding area, i.e., the fraction of the total sheet surface which is occupied by, e.g., calendered bonding points is usually higher for compact nonwovens than for high-loft nonwovens, as high bonding areas run counter high loft properties. Also the compaction settings, i.e., the settings for compacting the laid fibers that have been dispersed onto the belt, are different between typical standard and high loft products.

Compact nonwovens from linear fibers typically have a rather high tensile strength, particularly in machine direction ("MD"), i.e., in the direction of the moving belt, as the fibers are mainly oriented in MD, meaning that the mean fiber orientation is in MD. In high loft nonwovens, the tensile strength is generally lower, particularly in MD, but also in cross-machine direction ("CD") perpendicular thereto. The elasticity is usually higher in high loft nonwovens. The air permeability is usually lower in compact nonwovens, while high loft nonwovens have a softer feel. One disadvantage of the high barrier nonwovens, naturally, is the increased volume that is needed to ship the material.

One goal of the present invention is the provision of a spunbonded nonwoven fabric material which is high loft but does not exhibit all mechanical properties usually observed for high loft nonwoven fabric materials, and specifically has increased tensile strength.

Another goal of the invention is the provision of a spunbonded nonwoven fabric material which is high loft but can be adapted for shipping at low volume.

Another goal of the invention is the provision of a spunbonded nonwoven fabric material having a unique and soft touch and appearance.

Against this background the invention provides for a patterned spunbonded nonwoven fabric sheet comprising a plurality of spunbonded crimped fibers bonded together at a plurality of bonding points, wherein all fibers of the patterned spunbonded nonwoven fabric sheet are spunbonded crimped fibers. The fabric is characterized in that the configuration of the fibers within the sheet is inhomogeneous and varies according to a preferably regular pattern. The pattern is macroscopic in a sense that there are different macroscopic regions of different fiber configurations, the regions reach comprising a multitude of fibers following this configuration. The regions are preferably visible with the bare eye and may have a minimum size of, e.g., more than 10 mm$^2$.

In one embodiment the density of fibers and/or the mean orientation of the fibers of the fibers within the fabric sheet are inhomogeneous and vary according to the pattern. In one embodiment, also the mean crimp radius of the fibers can be inhomogeneous within the fabric sheet and vary according to the pattern. These are examples of how the configuration of the fibers may vary on a microscopic level in the different macroscopic regions.

The sheet may, for example, comprise two or more classes of distinct regions distributed over its area according to the pattern, one having a first fiber concentration (and hence material density as expressed in weight per volume) and another one having a second fiber concentration (and hence material density as expressed in weight per volume). For such fabrics there can be a definition of high and low density regions. The starting point of this definition is the average density of the fabric. Areas having a density higher than average can be considered high density areas and areas having a density lower than average can be considered low density areas. In one embodiment, there is one kind of high density regions and one kind of low density regions with more or less identical fiber densities. In one embodiment, the high density areas account for between 50 and 80% of the overall weight of the fabric.

The same applies in principle to mean fiber orientation and mean fiber crimp radius.

In one embodiment the pattern consists of parallel stripes oriented in machine direction of the sheet, wherein the stripes are preferably straight, sinus or zig-zag shaped. The stripes are preferably uninterrupted.

In one embodiment, the pattern is identical for the whole area of the sheet.

In one embodiment the sheet has a three-dimensional structure comprising a plurality of alternating elevations and depressions arranged according to the pattern. The three-dimensional patterned structure leads to a windy cross-sectional profile of the fabric sheet, meaning that when there is a protrusion on one surface of the sheet, there is an indentation on the other surface. For example, in the case where the pattern consists of parallel straight stripes, the fabric sheet may have a corrugated structure with grooves and crests oriented in one direction and a wavelike cross-section when cut along a direction perpendicular to the one direction.

In one embodiment, the elevations and depressions are high density regions and the transition zones between elevations and depressions are low density regions.

In embodiments where the sheet has a three-dimensional structure following the pattern, the vertical dimension of the structured fabric sheet exceeds the thickness of the sheet.

The factor may be, for example, at least two or at least three. The vertical dimension according to this definition corresponds to the mean distance between the highest point of elevations and the lowest point of depressions. The thickness of the sheet corresponds to the shortest distance between the upper and lower surface of the sheet at any particular spot on the surface.

In one embodiment, the thickness ("caliper") of the sheet remains essentially constant over the entire sheet surface, irrespective of differences in density or a three-dimensionally structured shape.

In one embodiment, the average density of the fabric is between 0.03 and 0.08 g/cm$^3$. In one embodiment, the average basis weight of the (potentially structured and not straightened) fabric is between 10 and 100 g/m$^2$. While these are average values, both the actual density and basis weight at a certain point on the surface of the fabric may vary according to the pattern.

In one embodiment, the ratio of tensile strength in machine direction ("TSMD") to tensile strength in cross-machine direction ("TSCD") is between 0.8 and 1.2 when measured according to WSP 110.4. This ratio is more balanced than typically observed for products of the prior art.

In one embodiment, the TSCD when measured according to according to WSP 110.4 of the sheet is within the boundaries as calculated by TSCD[$N$/50 mm]=basis weight [g/cm$^2$]*$A$ where A is between 0.7 and 1.3. This is higher than usually observed for high loft fabrics and would be more typical for compact fabrics.

In one embodiment the crimped fibers are crimped multicomponent fibers, where preferably one or all components are polymer components. For example, one or all components may comprise or consist of polypropylene. For example, components may consist of pure polypropylene, a polypropylene and polyethylene copolymer or a mixture of polypropylene and polyethylene homopolymers. Crimped multicomponent fibers comprise at least two zones asymmetrically distributed along their cross-section. The zones are constituted by different polymer materials, which are disparate in at least one physical property like melt elasticity, melt flow rate or the like. The distribution of the zones may be side-by-side, eccentric sheath-core or the like. Such fibers exhibit asymmetric behavior during drawing and quenching, which induces crimp. The technology to obtain crimped fibers is well-known in the art, e.g., from U.S. Pat. No. 6,454,989 B1.

Against the background as initially rendered, the invention further relates to a method for forming a spunbonded patterned nonwoven fabric sheet of any preceding claim, the method comprising: providing a flat spunbonded nonwoven fabric sheet starting material comprising a plurality of spunbonded crimped fibers bonded together at a plurality of bonding points, wherein all fibers of the patterned spunbonded nonwoven fabric sheet are spunbonded crimped fibers; and mechanically activating the starting material upon application of localized stretching forces to change the configuration of the fibers according to the pattern.

The mechanical activation causes deformation as bonds in the stretch zones are deactivated and the fiber structure becomes more open, meaning less dense. The fibers reorient themselves towards the direction of stretching. The fibers have a built in stretch capability due the, for example, helically crimped form or shape. It is thereby possible to stretch the in the Cross Machine (CD) with a so-called ring rolling process without shredding the material. If fibers of the starting material do not have any crimp the material would shred when trying to activate according to the invention. A certain amount of crimp in the individual fiber is needed in order to give the fibers enough extensibility to withstand the forces applied in the stretch zones during mechanical activation.

In one embodiment the steps of providing and activating the starting material are carried out at different sites remote from one another. The process of mechanical activation can take place directly after the formation of the flat nonwoven fabric sheet, in a remote standalone activation process or directly at the remote lines for the end use, e.g., for hygiene disposable manufacturing process. It is hence possible to ship a starting material which is comparatively low loft and activate the material only at the end use site to obtain a higher loft material, thereby saving on space needed for shipping and hence shipping cost.

In one embodiment, the step of mechanical activation includes ring rolling the flat nonwoven fabric sheet in a mill comprising a pair of interacting rolls each comprising a structured surface having elevations and depressions, wherein the surface structures and positions of the two rolls are such that elevations on the surface of one roll impinge onto corresponding depressions on the surface of the other roll. The structure on rolls is macroscopic and follows the fiber configuration pattern of the patterned nonwoven fabric sheet of the invention.

The surface structure of the rolls preferably exceeds the thickness of the flat nonwoven fabric sheet at least by factor two, three or five to impart a significant degree of mechanical activation.

In one embodiment the step of mechanical activation includes rolling the flat nonwoven fabric sheet in a mill comprising a pair of interacting rolls whose surfaces comprise interlocking annular grooves and crests. The annular grooves and crests constitute the elevations and depressions. This allows for producing an activated sheet of the invention where the pattern consists of parallel stripes oriented in machine direction. The elevations and depressions on the surfaces of the rolls may, for example, have a straight pathway along the circumference of the rolls or may adopt a sinus shaped or zig-zag shaped pathway, leading to either straight, sinus shaped or zig-zag shaped parallel stripes in the activated fabric.

The invention further relates to a flat spunbonded nonwoven fabric sheet starting material comprising a plurality of spunbonded crimped fibers bonded together at a plurality of preferably regularly distributed bonding points bonding points obtained from heat embossing, wherein all fibers of the flat spunbonded nonwoven fabric sheet are spunbonded crimped fibers. The flat sheet is characterized in that the number of bonding points per cm$^2$ of fabric surface is between 10 and 40 and preferably between 20 and 30, and in that the total area of bonding points is between 6 and 18% and preferably between 10 and 15% of the total area of the fabric.

In one embodiment the engraving depth of the bonding points is between 0.3 and 2.0 mm and preferably between 0.5 and 1.0. The engraving depth as understood herein corresponds to the penetration depth of the heat embossing structure, corresponding to, e.g., the height of the pins on the calender roll.

In one embodiment the quotient obtained by dividing the basis weight of the fabric sheet as expressed in grams per square meter (g/m$^2$) with the engraving depth of calender bonding as expressed in millimeters (mm) is between 20 and 150 and preferably between 40 and 90.

These bonding parameters/compaction settings are usually considered too tight for a high loft fabric and are hence not applied in the prior art to fabrics having crimped fibers. They are rather applied to fabrics having linear fibers.

The embossing is preferably obtained by application of a heated calender roll.

Of course, the bonding parameters are maintained during the process of the invention, such that the bonding parameters also apply to the patterned nonwoven fabric sheet according to the invention.

The parameters such as fibers, materials, average basis weight and density, caliper and the like of the flat nonwoven fabric sheet according to the invention can be as defined above for the patterned spunbonded nonwoven fabric sheet according to the invention.

The flat spunbonded nonwoven fabric sheet according to the invention is preferably used in a method of the invention to obtain a patterned spunbonded nonwoven fabric sheet according to the invention.

The patterned/activated spunbonded nonwoven fabric sheets of the invention can be used, for example, in the manufacture of hygiene products such as baby diapers, adult incontinence products or sanitary napkins. Other applications of the patterned/activated nonwoven fabric sheets of the invention include cleaning products like dust-off products and cleaning wipes, industrial products, air filtration products or medical products in general.

Figure 2:
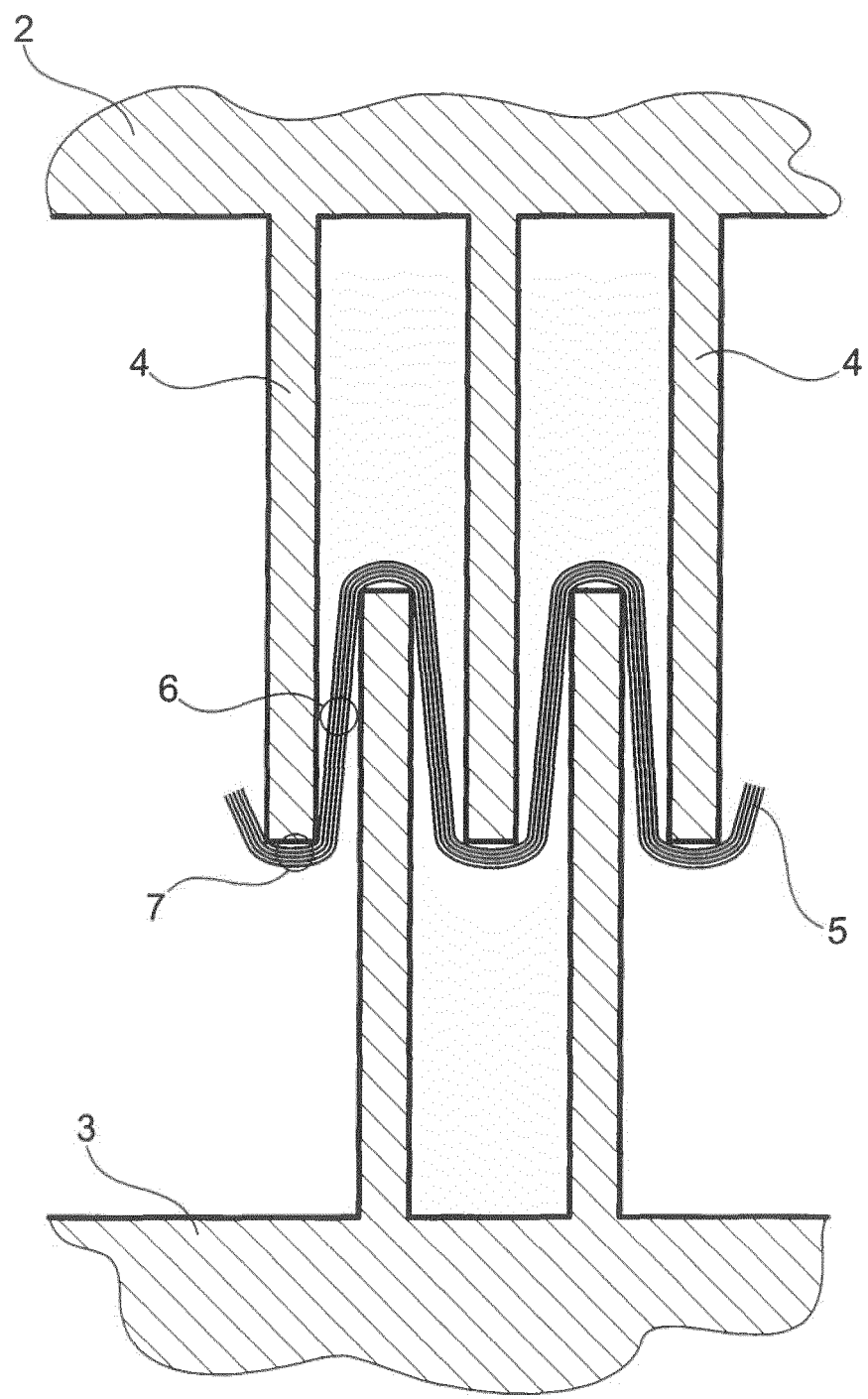

Further details and advantages of the invention are explained with reference to the figures and working examples described in the following. The figures show:

FIG. 1: an illustration of a mill configured to carry out a method according to the invention;

FIG. 2: an illustration of the mill of FIG. 1 in operation;

FIG. 3: enlarged top view pictures of an activated nonwoven fabric sheet according to the invention; and FIG. 4: enlarged perspective pictures of the sheet of FIG. 3; and FIG. 5: top view pictures of the fabric of FIG. 3 and two other nonwoven fabric sheets according to the invention of different basis weights.

FIG. 1 shows a mill 1 configured to carry out a method according to the invention. It comprises a pair of counter rotating rollers 2 and 3. Annular discs 4 are mounted to the surfaces of both rollers 2 and 3 to obtain a surface structure of annular grooves (between the discs) and crests (the discs). The discs 4 are mounted with an offset on rollers 2 and 3 and the discs 4 of one roller 2 or 3 interlock with the discs 4 of the other roller 3 or 2. In the working example, the width "a" of the discs 4 is 0.8 mm, the depth of engagement "b" ("DOE") is variable and the distance "c" between the discs 4 is 1.65 mm.

FIG. 2 shows the mill of FIG. 1 in operation. A flat nonwoven fabric sheet 5 comprising a plurality of crimped fibers bonded together at a plurality of bonding points is fed to the mill at a certain line speed and a corrugated pattern is worked into the nonwoven 5 by stretching in stress zones 6 while not stretching in stress-free zones 7.

The starting materials, i.e., the flat nonwoven fabric sheets used in different working examples were spunbonded polypropylene nonwovens made from crimped fibers in a side-by-side configuration with a regular PP homopolymer in combination with a PP/PE random copolymer at a distribution ratio of 50/50. The denier of the fibers was 1.8. All materials were open dot bonded at 24 dots/cm$^2$ by calender bonding at an engraving depth of 0.75 mm to obtain a bonding ratio of 12.1%. The starting materials had the characteristics as described in Table 1.

TABLE 1

| Material # | Basis weight [g/m$^2$] | Caliper[1] [mm] | Density [g/cm$^3$] | Quotient[2] |
|---|---|---|---|---|
| A | 99.9 | 0.75 | 0.133 | 133.2 |
| B | 50.5 | 0.63 | 0.0802 | 67.3 |
| C | 21.0 | 0.39 | 0.0538 | 28.0 |

| Material # | TSMD[3] [N/50 mm] | TEMD[4] [%] | TSCD[5] [N/50 mm] | TECD[6] [%] |
|---|---|---|---|---|
| A | 75.8 | 62.5 | 55.2 | 108.0 |
| B | 65.2 | 93.6 | 37.8 | 117.7 |
| C | 28.2 | 85.6 | 14.6 | 97.7 |

[1]Caliper: Thickness of the material according to WSP.120.1 (R4)
[2]Quotient: Quotient obtained by dividing the basis weight [g/m$^2$] with the engraving depth of calender bonding [mm]
[3]TSMD: Tensile strength in MD according to WSP 110.4
[4]TEMD: Tensile elongation in MD according to WSP 110.4
[5]TSCD: Tensile strength in CD according to WSP 110.4
[6]TECD: Tensile elongation in CD according to WSP 110.4

These starting materials were activated in a mill as shown in FIG. 1 in a process as shown in FIG. 2. The settings were as shown in Table 2.

TABLE 2

| Example # | Material # | DOE [mm] | Line speed [m/min] |
|---|---|---|---|
| 1 | A | 3.0 | 20 |
| 2 | B | 4.0 | 10 |
| 3 | B | 4.0 | 20 |
| 4 | B | 4.0 | 30 |
| 5 | B | 2.0 | 20 |
| 6 | C | 5.0 | 20 |

The resulting materials had the characteristics as described in Table 3.

TABLE 3

| Example # | Basis weight [g/m$^2$] | Caliper [mm] | Density [g/cm$^3$] |
|---|---|---|---|
| 1 | 66.6 | 1.37 | 0.0486 |
| 2 | 26.9 | 0.820 | 0.0328 |
| 3 | 25.9 | 0.818 | 0.0320 |
| 4 | 27.3 | 0.874 | 0.0312 |
| 5 | 43.9 | 0.602 | 0.0729 |
| 6 | 11.0 | 0.320 | 0.0344 |

| Example # | TSMD [N/50 mm] | TEMD [%] | TSCD [N/50 mm] | TECD [%] |
|---|---|---|---|---|
| 1 | 37.4 | 56.0 | 30.2 | 72.2 |
| 2 | 19.8 | 45.1 | 19.4 | 91.8 |
| 3 | 18.6 | 48.0 | 18.2 | 94.5 |
| 4 | 23.3 | 98.0 | 18.3 | 47.8 |
| 5 | 48.9 | 91.9 | 35.3 | 83.7 |
| 6 | 6.8 | 59.0 | 6.4 | 28.8 |

Figure 3A:
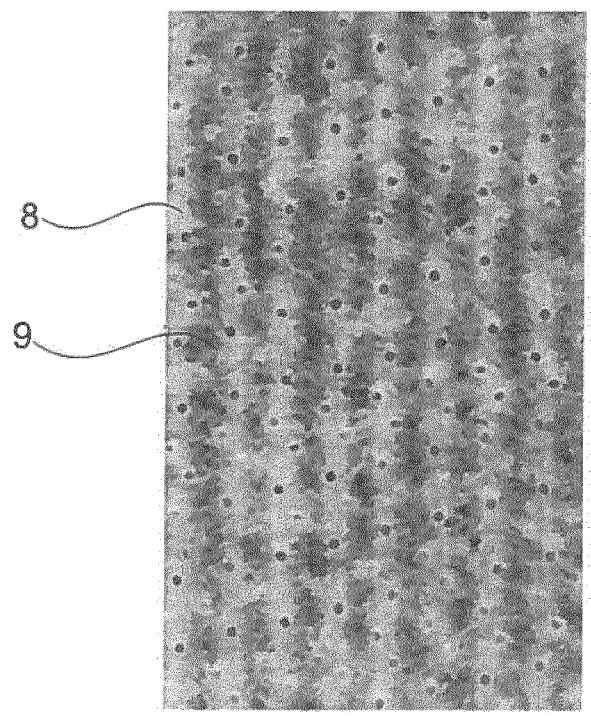

FIG. 3a shows a top view picture of the inventive nonwoven fabric sheet of Example 3. The material has a corrugated three-dimensional structure with grooves and crests oriented in longitudinal direction (MD) and a wave-like cross-section when cut in a direction perpendicular thereto (CD). It can be seen that the fiber structure within the material has been rearranged and is inhomogeneous. It varies according to the corrugated pattern.

There are longitudinal (MD) stripes 8 with a high fiber density and a mean fiber orientation in MD. These stripes appear brighter in the picture and extend longitudinally (in MD) in the top areas of the crests and the bottom areas of the valleys. The areas corresponding to these stripes 8 have not or hardly been stretched during the activation process. They correspond to the stress-free zones 7 of FIG. 2.

The stripes 8 are interrupted by longitudinal (MD) stripes 9 of lower fiber density and a mean fiber orientation in CD. These stripes appear darker in the picture and extend longitudinally (in MD) in the transition zones between crests and valleys. The areas corresponding to these stripes 9 have significantly been stretched during the activation process. They correspond to the stress zones 6 of FIG. 2.

Figure 3B:
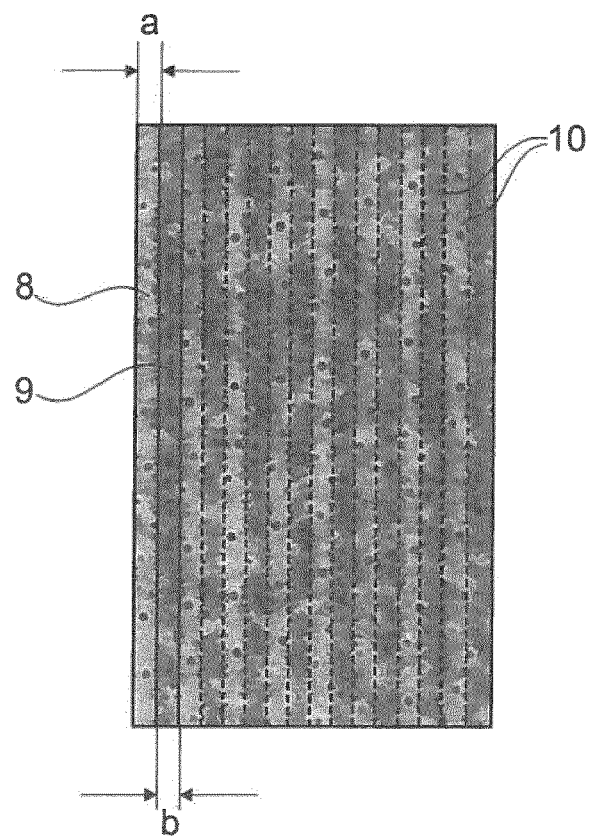

To determine the fiber concentration in the high concentration areas 8 and the low concentration areas 9, the sheet of Example 3 has been sliced in longitudinal stripes as shown in FIG. 3b. The cutting lines are marked with reference numeral 10 and extend longitudinally (in MD) along the boundaries between areas 8 and 9. The cutting lines 10 where chosen such that all strips had an equal width, meaning that the width of all strips corresponding to the areas 8 was equal to the width of all strips corresponding to the areas 9. This allowed a comparative analysis by simple weighting of the materials. In one step, all strips corresponding to the areas 8 were weighed. In another step, all strips corresponding to the areas 9 were weighted. The result was that the high concentration areas 8 account for 61.7% of the overall weight of the sample and the low concentration areas 9 account for 38.3% of the overall weight of the samples.

Figure 4A:
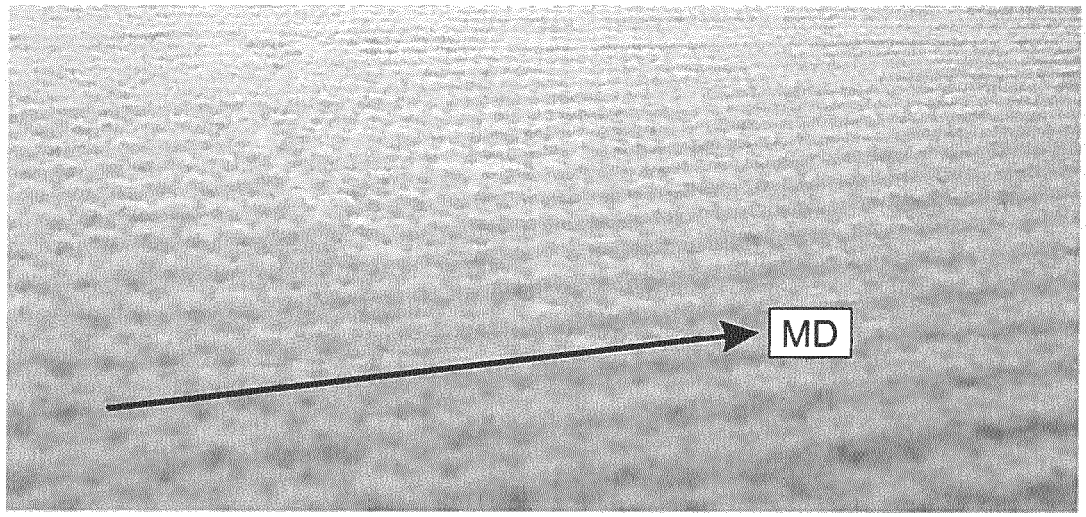
Figure 4B:
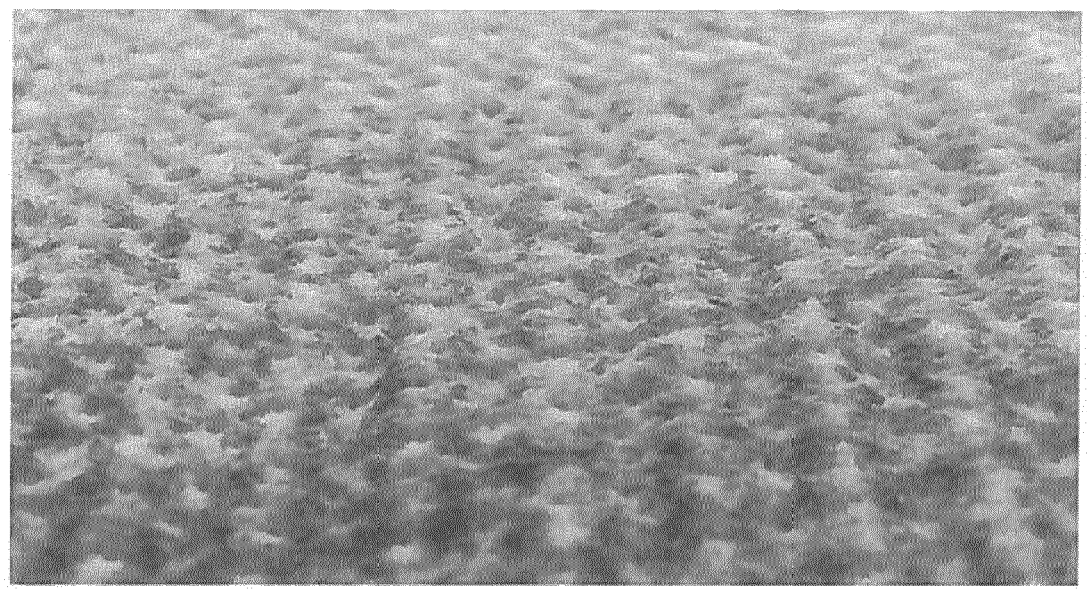

As apparent from FIGS. 4a and 4b, the activated fabric of Example 3 has a textile-like appearance, which can be desirable in certain applications, for example, hygiene applications.

Figure 5A:
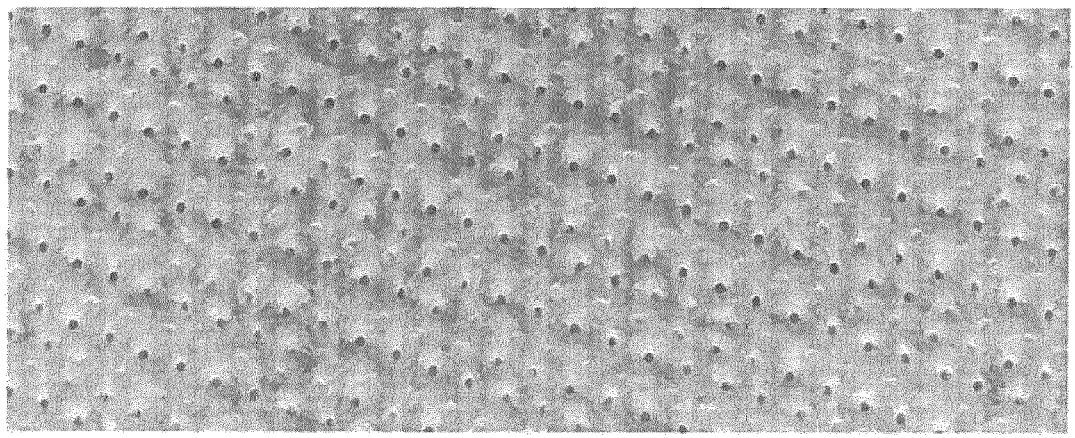
Figure 5B:
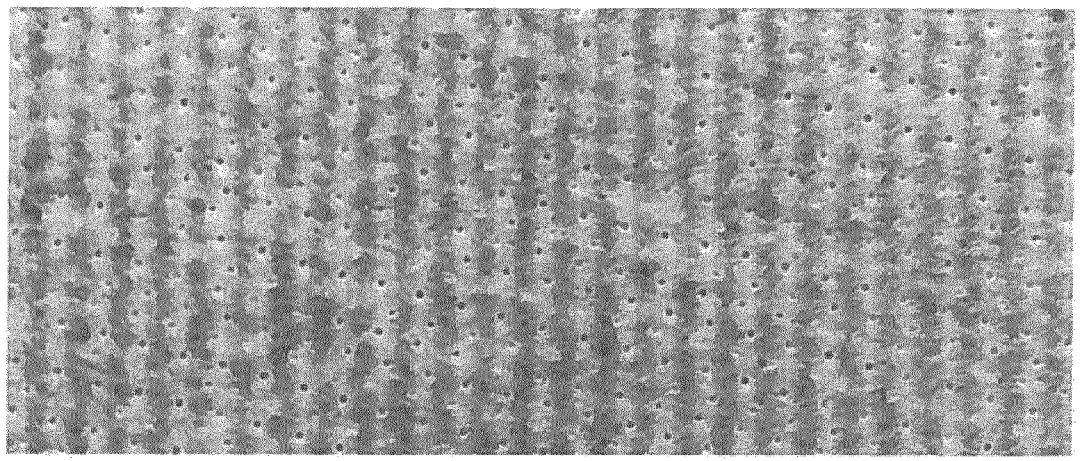
Figure 5C:
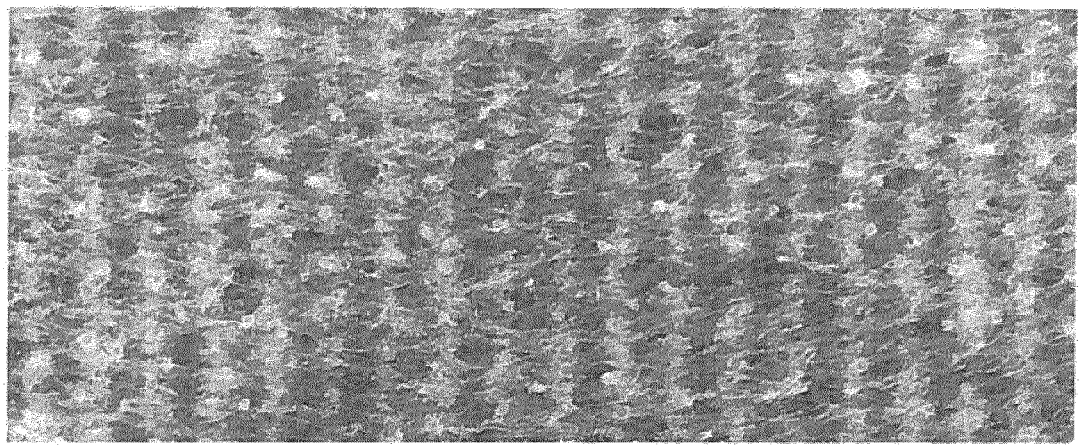

FIGS. 5a to 5c show top view pictures the nonwoven fabrics of Example 1 (FIG. 5a), again Example 3 (FIG. 5b) and Example 6 (FIG. 5c). As apparent from these illustrations, activation according to the invention can be observed in all examples. Different qualities of activation are observed. When using the dense starting material as in Example 1, the web does not open up as readily during activation as when using a more open fabric as in Example 3. On the other hand, when using a very open fabric as in Example 6, the high and low density areas in the activated fabric are not as emphasized.

The invention claimed is:

1. A patterned spunbonded nonwoven fabric sheet comprising a plurality of spunbonded crimped fibers bonded together at a plurality of bonding points, wherein all fibers of the patterned spunbonded nonwoven fabric sheet are spunbonded crimped fibers,
   wherein a density of fibers, or a mean orientation of the fibers, or a mean crimp radius of the fibers within the fabric sheet, or any combination thereof, are inhomogeneous and varies according to a regular pattern,
   wherein the regular pattern is such that the fabric sheet has a three-dimensional structure comprising a plurality of alternating elevations and depressions arranged according to the regular pattern,
   wherein the three-dimensional structure is such that a cross-sectional profile of the fabric sheet in a cross-machine direction thereof is windy such that when there is an elevation on one surface of the fabric sheet, there is a depression on another surface of the fabric sheet corresponding to each elevation,
   wherein the fabric sheet comprises high-density areas having an above average fiber density of the fabric sheet, and low-density areas having a below average fiber density of the fabric sheet,
   wherein the plurality of alternating elevations and depressions are the high density areas and transition zones between the plurality of alternating elevations and depressions are the low-density areas,
   wherein the regular pattern comprises parallel, uninterrupted, straight stripes oriented in a machine direction of the fabric sheet and said regular pattern is irrespective of the plurality of bonding points present, and
   wherein each of the parallel, uninterrupted, straight stripes is a continuous stripe from one end of the fabric sheet to another end of the fabric sheet.

2. The patterned spunbonded nonwoven fabric sheet according to claim 1, wherein the high-density areas account for between 50 and 80% of the overall weight of the fabric sheet.

3. The patterned spunbonded nonwoven fabric sheet according to claim 1, wherein the crimped fibers are crimped multicomponent fibers.

4. The patterned spunbonded nonwoven fabric sheet of claim 3, wherein one or all components of the crimped multicomponent fibers are polymer components.

5. The patterned spunbonded nonwoven fabric sheet of claim 3, wherein one or all components of the crimped multicomponent fibers comprise polypropylene.

6. A method for forming a patterned spunbonded nonwoven fabric sheet of claim 1, the method comprising:
   providing a flat spunbonded nonwoven fabric sheet starting material comprising a plurality of spunbonded crimped fibers bonded together at a plurality of bonding points, wherein all fibers of the patterned spunbonded nonwoven fabric sheet are spunbonded crimped fibers; and
   mechanically activating the starting material upon application of localized stretching forces to change the configuration of the fibers according to the pattern.

7. The method of claim 6, wherein the steps of providing and mechanically activating the starting material are carried out at different sites remote from one another.

8. The method of claim 6, wherein the step of mechanically activating includes rolling the flat spunbonded nonwoven fabric sheet starting material in a mill comprising a pair of interacting rolls whose surfaces comprise interlocking annular grooves and crests.

* * * * *